United States Patent [19]
Kelly et al.

[11] Patent Number: 5,908,753
[45] Date of Patent: Jun. 1, 1999

[54] TRANSFORMATION OF *CANDIDA ALBICANS* BY ELECTROPORATION

[75] Inventors: Rosemarie Kelly, Westfield; Elizabeth A. Register, Watchung; Myra B. Kurtz, Martinsville; John R. Thompson, Scotch Plains, all of N.J.

[73] Assignee: Merck & Co., Inc., Rahway, N.J.

[21] Appl. No.: 08/932,003

[22] Filed: Sep. 17, 1997

Related U.S. Application Data

[60] Provisional application No. 60/027,772, Oct. 4, 1996.

[51] Int. Cl.$^6$ .......................................... C12Q 1/68

[52] U.S. Cl. ...................... 435/6; 435/172.3; 435/254.22

[58] Field of Search ........................ 435/6, 172.3, 254.22

[56] References Cited

PUBLICATIONS

Mol. Gen. Genet, vol. 251, pp. 75–80 (1996), by D. H. Brown, Jr., et al.
Mol. Gen. Genet, vol. 214, pp. 24–31 (1988), by R. Kelly, et al.
Molecular & Cellular Biology, vol. 7, No. 1, pp. 199–207 (1987), by R. Kelly, et al.
Molecular & Cellular Biology, vol. 7, No. 1, pp. 209–217 (1987), by M. B. Kurtz, et al.
Molecular & Cellular Biology, vol. 6, No. 1, pp. 142–149 (1986), by M. B. Kurtz, et al.

*Primary Examiner*—James Ketter
*Attorney, Agent, or Firm*—Elliott Korsen; Mark R. Daniel

[57] ABSTRACT

There is disclosed a procedure for DNA-mediated transformation of *Candida albicans* by electroporation utilizing lithium acetate and dithiothreitol to weaken the cell wall structure and optimize the yield of transformants.

6 Claims, 1 Drawing Sheet

TRANSFORMATION OF *CANDIDA ALBICANS* BY ELECTROPORATION

This application claims the benefit of U.S. Provisional Application Ser. No. 60/027,772, filed Oct. 4, 1996

FIELD OF THE INVENTION

The present invention relates to a procedure for DNA-mediated transformation of *Candida albicans* by electroporation. More particularly, the invention relates to the treatment of the host strain with lithium acetate and dithiothreitol in order to weaken the cell wall structure and optimize the yield of transformants.

BACKGROUND OF THE INVENTION

Electroporation has become the preferred method for gene transfer due to its ease and efficiency of operation in comparison to alternate techniques. To date, electroporation has been utilized to transform a wide variety of cell types including mammalian cells, plant protoplasts, bacteria and fungi, including yeast. The technique involves subjecting cells to a high voltage electric field, which results in the temporary formation of pores in the membrane, thereby allowing exogenous DNA to enter the cells. For example, laboratory strains of the yeast *Saccharomyces cerevisiae* have been transformed by electroporation with either self-replicating plasmids or by integration of linearized plasmid DNA into the host genome.

*Candida albicans* is a pathogenic, diploid yeast capable of causing a broad spectrum of infections, especially in immunocompromised individuals. As the number of persons with increased susceptibility to *Candida* has risen over the past decade, so has the importance of this organism as an agent of disease. Much work has been done on this organism to identify potential virulence factors and to study its biology. To further the understanding of *C albicans* biology at the molecular level, a number of transformation systems have been developed. Integrative transformation was the first method developed for the transformation of *C. albicans* (Kurtz et al., Mol. Cell. Biol. (1986) 6:142–149). It is now widely used for genetic manipulation. Other references regarding transformation of *Candida albicans* include Kelly et al. Mol. Cell. Biol. (1987) 7:199–207; Kurtz et al. Mol. Cell. Biol. (1987) 7:209-217; Kelly et al. Mol. Gen. Genet. (1988) 214:24–31; Cannon et al., Mol.. Gen. Genet. (1990) 235:4453–457; A recent journal article, Brown et al., Mol. Gen. Genet. (1996) 251:75–80, discloses a transformation method for *C. albicans* using restriction enzyme-mediated integration.

SUMMARY OF THE INVENTION

The present invention relates to a process for the transformation of *Candida albicans* for use as a preclinical and clinical research tool. The invention also relates to the use of the transformed host to develop screens to detect new drugs and to study the mode of action of existing drugs.

DETAILED DESCRIPTION OF THE INVENTION

Figure 1:
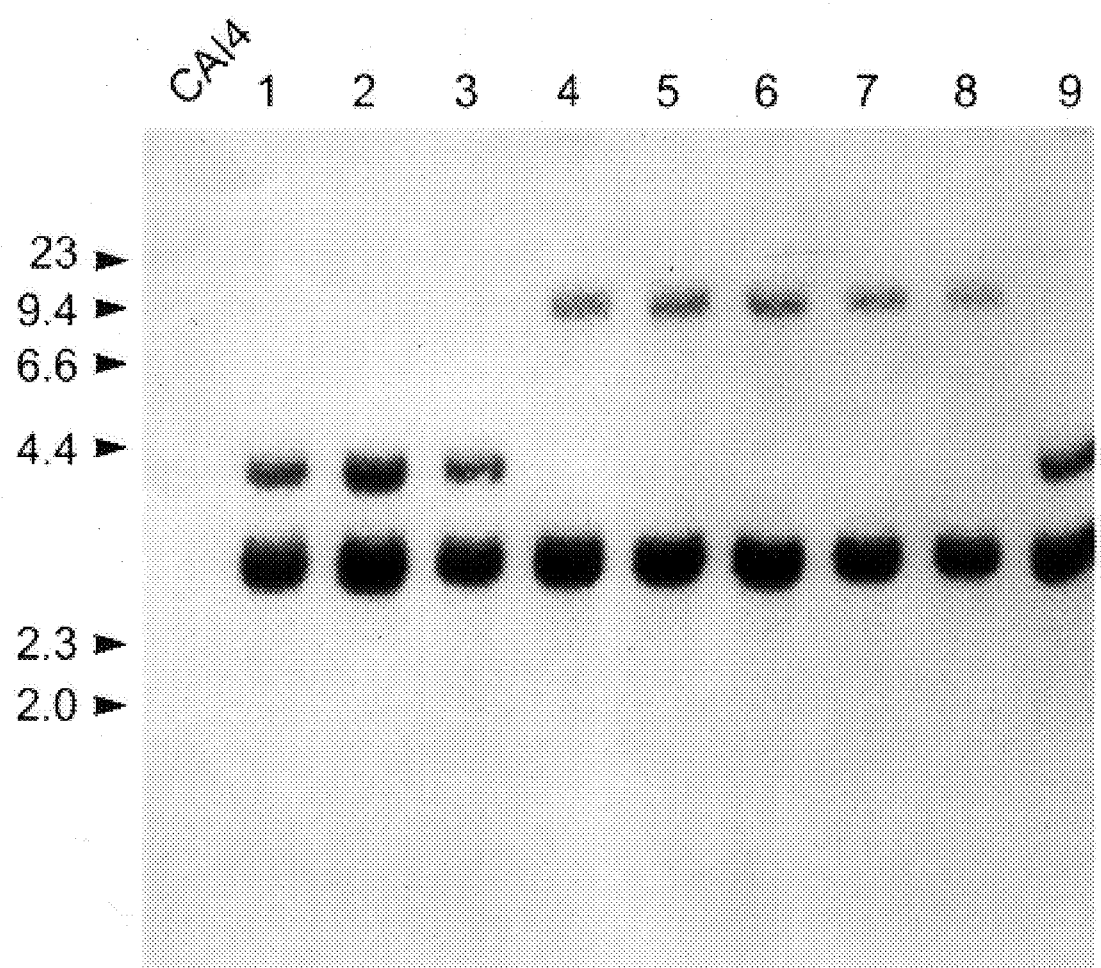
FIG. 1 represents an autoradiogram of Southern blot hybridization of Ura+transformants. Lane containing parent strain CAI4 is indicated. Ura+transformants 1–8 were obtained with a HpaI digest of pJAM11 and transformant 9 was obtained with circular pJAM11. Lambda DNA digested with *Hind*III was included as molecular size standards.

The present invention relates to a novel process for the transformation of *Candida albicans* by electroporation. More particularly, the invention relates to the treatment of the host strain with lithium acetate and dithiothreitol in order to to weaken the cell wall structure and optimize the yield of transformants.

The first aspect of the invention relates to the process which comprises (1) treating the host strain (a ura3 mutant in this example) with lithium acetate/dithiothreitol; (2) adding plasmid DNA containing a selectable transformation marker (the URA3 gene in this example) to the treated host strain; (3) introducing said DNA construct into the host strain by application of an electrical pulse to form transformed cells; and (4) selecting said transformed cells, in this case, by their ability to grow in selective medium lacking uracil/uridine.

A second aspect of the invention relates to the introduction of other genes encoding potential antifungal targets into *Candida*.

A third aspect of the invention relates to the use of the transformed host strains as a preclinical and clinical tool. The transformed *C. albicans* can be used to study mode of action of antifungals as well as to evaluate potential resistant mechanisms. They can also be used for developing screens to detect new drug candidates. In particular, a method of using the transformed host strains to construct a two plate screen for new antibiotics in which one strain is an underproducer of a given antifungal target and the other strain is an overproducer of the target is contemplated.

A fourth aspect of the invention relates to the molecular manipulation of *C. albicans* for gene cloning, gene analysis, and gene disruption experiments.

While DNA-mediated transformation of *C. albicans* has been achieved in the past, none of the prior methods are particularly efficient. DNA-mediated transformation has been achieved by a spheroplasting method (Kurtz et al., Mol. Cell Biol. [1986] 7:142–149) but this necessitates the time-consuming step of protoplast formation. DNA-mediated transformation of *C. albicans* has also been accomplished by a lithium acetate protocol (Kurtz, M. and Scherer, S., in *More Gene Manipulations in Fungi*, Bennett, J. and Lasure, L., Eds., Academic Press Inc., San Diego, Calif. [1991], p.342–363), but circular DNA transforms *C. albicans* poorly as the vectors do not contain an autonomously replicating sequence that is as efficient as the *S. cerevisiae* 2 micron element. Thus, this technique necessitates performing many transformation reactions in order to obtain the desired number of transformants. This is time consuming and requires a large quantity of DNA.

The following examples are provided to illustrate the invention but are not to be construed as limiting the scope of the invention.

Strains and DNA were isolated and handled by standard procedures [J. Sambrook, E. F. Fritsch, and T. Maniatis, "Molecular Cloning, A Laboaratory Manual", second edition, Cold Spring Harbor Laboratory Press, Cold Spring Harbor, N.Y. (1989)], referred to as Maniatis. Many of the procedures for working with *S. cerevisiae* are described in M. D. Rose, F. Winston, and P. Hieter, "Methods in Yeast Genetics: a Laboratory Course Manual", Cold Spring Harbor Laboratory Press, Cold Spring Harbor, N.Y. (1990), referred to as MYG.

EXAMPLE 1

ELECTROPORATION OF WHOLE CELLS

The host strain used for transformation is a *C. albicans* ura3 mutant, CAI4, which contains a deletion of orotidine- 5'-phosphate decarboxylase and was obtained from William Fonzi, Georgetown University (Fonzi and Irwin, Genetics [1993] 134:717–728). The selectable marker for transformation is the C. albicans URA3 gene which was isolated as described below. The protocol for electroporation is similar to the S. cerevisiae procedure of Becker and Gurarente, 1991, with the inclusion of an incubation in 100 mM lithium acetate/10 mM dithiothreitol (DTT)/TE (TE is 10 mM TrisHCl pH 7.5, 1 mM EDTA) prior to electroporation. It is believed that lithium acetate can be used in the range of about 75 to about 125 mM and DTT can be used in a range of about 10 to about 100 mM.

Cloning of C. albicans URA3 gene

The C. albicans URA3 gene was independently cloned by complementation of a S. cerevisiae ura3 mutant in the same manner that it was previously isolated by Gillum et al. (Mol. Gen. Genet. [1984] 198:179–182). The library used for complementation contains Sau3A partial digests of genomic DNA (Rosenbluth et al., Mol. Gen. Genet. [1985] 200:500–502) prepared from strain B792 (Kwon-Chung, K. J., and Hill, W. B., [1979] Sabouraudia 8:48–59) cloned in vector YEp13. YEp13 is a LEU2 $2\mu$ plasmid, Broach et al., Gene [1979] 8:121–133. The ura3 mutant used for complementation was W303-1A (mat a, ura3-1, leu2-2,112, his3-11, trp1-1, ade2-1). W303-1A was transformed to Leu$^+$ with the library by standard spheroplasting techniques (MYG). Leu$^+$ transformants were selected on synthetic medium osmotically stabilized with 1 M sorbitol and supplemented with 0.2% each histidine, tryptophan, uracil, and adenine. Synthetic medium is Yeast Nitrogen Base without amino acids (Difco) supplemented with 2% glucose and solidified with 2% agar. The Leu$^+$ transformants were harvested and subsequently plated on similar medium, only uracil was omitted instead of leucine. Four Ura$^+$ Leu$^+$ transformants were subsequently purified on the same medium. Plasmid DNA was isolated from the four Ura$^+$ Leu$^+$ transformants (MYG) and introduced into E. coli RR1 (Bolivar et al., Gene [1977] 2:95–113; obtained from Gibco-BRL). Plasmid DNA was prepared from ampicillin resistant E. coli by a miniprep DNA procedure (Maniatis). Restriction digestion of the plasmid DNA with XbaI indicated that three out of four plasmids had a fragment ~4.5 kb consistent with the published restriction map of the URA3 locus. This plasmid was designated pJAM5. Additional restriction mapping confirmed that pJAM5 contained the URA3 locus from C. albicans. Retransformation of pJAM5 into W303–1A restored the Ura$^+$ phenotype. A subclone containing the URA3 gene, pJAM11, was constructed by inserting an ~4.5 kb XbaI—XbaI fragment from pJAM5 containing the URA3 gene into vector pUC18 (Yanisch-Perron et. al., Gene [1985] 33:103–119; obtained from BRL) using methods known to the art as described by Maniatis.

ELECTROPORATION PROTOCOL a) Growth of yeast cells:

A loop of cells is inoculated into 50 ml of YPAD broth containing 200 $\mu$l 0.1 M uridine and is grown overnight at 30° C. to stationary phase. YPAD broth contains 2% peptone, 1% yeast extract (both from Difco), 2% glucose and 0.8% adenine. The $A_{600}$ nm is measured and ~0.1 O.D. units are inoculated into 100 ml of YPAD broth plus 400 $\mu$l of 0.1 M uridine. The culture is grown overnight and harvested at an $A_{600}$nm of ~1.3.

b) Harvesting of yeast cells:

The cells are collected by centrifugation at 5000 rpm and the pellet is resuspended in 25 ml of 100 mM lithium acetate/10 mM dithiothreitol/TE and incubated at room temperature for one hour. Next, the cells are collected by centrifugation at 5000 rpm for 5 min at 4° C. and the pellet is resuspended in 25 ml ice-cold water. This step is repeated one time and the pellet is resuspended in 10 ml of ice-cold 1 M sorbitol. The mixture is transferred to a chilled 15 ml polypropylene centrifuge tube and centrifuged at 5000 rpm for 5 min at 4° C. The supernatant is carefully removed, and the pellet is resuspended in 100 $\mu$l of 1 M sorbitol and held on ice.

c) Electroporation:

For each transformation, forty microliters of cells are aliquoted to a microfuge tube. Plasmid DNA is prepared from ampicillin-resistant E. coli using the QIAGEN-tip 500 procedure (QIAGEN Inc., Chatsworth, Calif.). The DNA is added (0.5 $\mu$g for linearized plasmid DNA and 1.0 $\mu$g for circular plasmid DNA) and the mixture is incubated on ice for about five minutes. The mixture is transferred to a cold 0.2 cm electroporation cuvette. The cuvette is placed in the electroporation chamber and is pulsed at 1.5 kV, 25 $\mu$FD, 200 ohms. The cuvette is removed and 1 ml cold 1 M sorbitol is added immediately and the contents of the cuvette are mixed by inversion. One hundred microliter aliquots are plated onto selective synthetic medium which is Yeast Nitrogen Base without amino acids (Difco) supplemented with 2.0% glucose and 0.87% -Ura dropout powder. The composition of -Ura dropout powder is shown in Table 1. The medium is solidified with 2.0% agar. The plates are incubated at 30° C. for 4–5 days.

TABLE 1

| Ura Dropout Powder | |
|---|---|
| Adenine | 0.8 g |
| L-Arginine | 0.8 g |
| L-Aspartic acid | 4.0 g |
| L-Histidine | 0.8 g |
| L-Isoleucine | 1.2 g |
| L-Leucine | 2.4 g |
| L-Lysine | 1.2 g |
| L-Methionine | 0.8 g |
| L-Phenylalanine | 2.0 g |
| L-Threonine | 8.0 g |
| L-Tryptophan | 0.8 g |
| L-Tyrosine | 1.2 g |
| L-Valine | 6.0 g |

Mix with a mortar and pestle d. Results

The results from a typical electroporation experiment with plasmid pJAM11 are shown in Table 2. Both circular and linearized pJAM11 were transformed into ura3 mutant CAI4. Digestion of pJAM11 with restriction enzyme HpaI linearizes the plasmid and provides a site for targeted integration of the DNA into the genome of CAI4 via homologous recombination. The effect of incubation with and without lithium acetate/DTT/TE is also shown in this Table.

The transformation frequency obtained in the presence of the lithium acetate/DTT/TE incubation was 142 transformants/$\mu$g DNA with a HpaI digest of pJAM11 and 3/$\mu$g DNA with circular pJAM11. It has previously been shown that linearization of the transforming DNA yields a 10–100-fold increase in the transformation frequency (Kurtz et al.,1986; Kelly et al.,1987, supra). All of the numerous transformants tested grew upon subsequent streaking to synthetic medium (medium described above). It surprisingly was found that the incubation in 100 mM lithium acetate/10 mM dithiothreitol/TE resultrd in an approximately 3-fold increase in the transformation frequency with linearized pJAM11 (the precise fold-increase with circular DNA cannot be calculated because no transformants were obtained in the absence of the lithium acetate/DTT/TE incubation). Incubation for a longer time, i.e., overnight in lithium acetate/DTT/TE followed by electroporation did not yield any transformants. No transformants were obtained in the absence of electroporation showing the importance of the electroporation step itself. We have obtained an average transformation frequency of 254 transformants/µg DNA with linearized pJAM11, and 3 transformants/µg DNA with circular pJAM 11. No enhancement of the transformation frequency was obtained by plating the electroporated cells on synthetic medium containing 1 M sorbitol as osmotic stabilizer.

TABLE 2

Effect of LiAc/DTT/TE Incubation on Transformation Frequency (# transformants/µg DNA)

| Reaction Conditions | Linear DNA pJAM11 (HpaI) | Circular DNA (pJAM11) |
|---|---|---|
| Control[a] | 142 | 3 |
| No DTT | 14 | 0 |
| No LiAc | 96 | 2 |
| No LiAc/DTT | 44 | 0 |
| No Electroporation | 0 | 0 |

[a]Contains lithium acetate/DTT/TE

SOUTHERN BLOT ANALYSIS

To further confirm that plasmid DNA had been introduced into CAI4 by electroporation, Southern blot analysis was performed. Genomic DNA was isolated from CAI4 and from nine Ura+ transformants of CAI4 using methods known to the art (MYG). The genomic DNAs were digested with EcoRI and the resultant fragments were separated by agarose gel electrophoresis and transferred to a Zeta-Probe GT quaternary amine derivatized nylon membrane (manufactured by BioRad). The blot was hybridized with a radiolabeled ($^{32}$P) 1.5 kb XbaI-ScaI fragment isolated from pJAM11. The 1.5 kb XbaI-ScaI fragment was radiolabeled by random priming (Feinberg and Vogelstein (1983) Anal. Biochem, 132, 6–13) and the blot was hybridized using conditions recommended for Zeta membranes by the manufacturer Biorad. As shown in FIG. 1, no hybridization was obtained to DNA from parent strain CAI4 which has a complete deletion of the 1.5 kb XbaI-ScaI fragment used as probe. In contrast, hybridization was obtained with DNA from all of the Ura+ transformants tested. This result confirms that the URA3 gene has been transformed into CAI4 by electroporation. In all of the transformants an ~3.0 kb EcoRI fragment internal to pJAM 11 was detected. In addition, an EcoRI fragment of either ~4.0 kb or ~12.0 kb was detected. These fragment sizes are consistent with integration of pJAM11 into either of the two alleles containing the URA3 locus which can be distinguished by an EcoRI restriction site polymorphism (Kelly et al., 1987; supra).

The stage of growth at which the cells are harvested for electroporation has an effect on the transformation frequency and it has been observed for S. cerevisiae that even a slight change in the $A_{600}$ nm that the cells are harvested at, can have a marked effect on the transformation frequency. An experiment to address this was performed. Cells harvested at four different $A_{600}$ nm determinations, 0.75, 1.0. 1.3, and 1.6, were electroporated with both linearized and circular pJAM11. Cells harvested at an $A_{600}$ nm of 1.3 gave the highest transformation frequencies; the frequency for linearized pJAM11 was 440/µg while that for circular was 5/µg in this experiment.

An experiment to optimize the plasmid DNA concentration indicated that an amount of DNA less than or equal to 0.2 µg would yield the highest frequency of transformants per µg DNA. However, with lower amounts of DNA, the number of transformants may not be significant. Thus, we obtain optimum numbers of transformants per electroporation with 0.2–0.5 µg of linearized plasmid DNA and 1.0–2.0 µg of circular plasmid DNA.

EXAMPLE 2

ELECTROPORATION OF PROTOPLASTS

It is possible that electroporation of protoplasts will yield higher transformation frequencies for circular DNA which may not penetrate the cell wall efficiently. Protoplasts were formed as described previously for S. cerevisiae (Beggs, Nature [1978] 275:104–1090) and the resulting protoplasts were resuspended in CAS (1 M sorbitol, 10 mM $CaCl_2$, 10 mM Tris pH 7.5). The protoplasts were electroporated at 1.0 kV, 25 µFD, 200 ohms with linearized and circular pJAM11. Plasmid pJAM11 was described in the previous example. The transformation frequency for linearized and circular pJAM11 was 40/µg and 1/µg, respectively. The results suggest that it should be possible to improve transformation frequencies of protoplasts with circular DNA by modification of the electroporation conditions.

What is claimed is:

1. A method for transforming *Candida albicans* comprising the steps of a) treating said *Candida albicans* host strain with lithium acetate and dithiothreitol to produce a treated host strain;

b) adding plasmid DNA containing a selectable transformation marker to the treated host strain;

c) introducing said plasmid DNA into the host strain by application of an electrical pulse to form transformed cells; and d) selecting said transformed cells.

2. The method of claim 1 wherein the host strain is a ura3 mutant.

3. The method of claim 1 wherein the selectable transformation marker is the URA3 gene.

4. The method of claim 1 wherein the transformed cells are selected by their ability to grow in selective medium lacking either uracil or uridine.

5. The method of claim 1 wherein about 75–125 mM lithium acetate is employed.

6. The method of claim 1 wherein about 10–100 mM dithiothreitol is employed.

* * * * *